United States Patent [19]
Dimeff

[11] 3,943,368

[45] Mar. 9, 1976

[54] METHOD AND APPARATUS FOR COMPENSATING REFLECTION LOSSES IN A PATH LENGTH MODULATED ABSORPTION-ABSORPTION TRACE GAS DETECTOR

[75] Inventor: John Dimeff, San Jose, Calif.

[73] Assignee: The United States of America as represented by the United States National Aeronautics and Space Administration Office of General Counsel-Code GP, Washington, D.C.

[22] Filed: Oct. 15, 1974

[21] Appl. No.: 514,546

[52] U.S. Cl. .................................. 250/573; 250/343
[51] Int. Cl.² ........................................ G01N 21/26
[58] Field of Search ............ 250/573, 574, 339, 343; 356/201, 204, 207, 208, 96

[56] References Cited
UNITED STATES PATENTS

| | | | |
|---|---|---|---|
| 3,679,899 | 7/1972 | Dimeff ............................. | 250/343 |
| 3,711,708 | 1/1973 | Dolin et al. ...................... | 356/96 |
| 3,805,074 | 4/1974 | McCormack ..................... | 250/573 |
| 3,851,176 | 11/1974 | Jeunehomme et al. ............ | 250/343 |

*Primary Examiner*—Eli Lieberman
*Assistant Examiner*—D. C. Nelms
*Attorney, Agent, or Firm*—Darrell G. Brekke; Armand G. Morin, Sr.; John R. Manning

[57] ABSTRACT

A method and apparatus is described for compensating for reflection losses in an optical path length modulated absorption-absorption gas analyzer used for determining the density of a reference gas in an unknown gas sample. The apparatus comprises a first chamber for containing a first gas including a reference gas at a known partial density and a second chamber for containing a second gas including a sample of the reference gas at an unknown partial density. A source of radiant energy is provided for passing radiant energy through the first and second chambers. Means are provided for modulating the path length of the radiant energy in the chambers. Additionally, a chopper wheel comprising a plurality of gas cells containing a sample of the reference gas is interspersed by a plurality of gas cells containing a gas excluding the reference gas. The chopper wheel is provided between the first and the second chambers and a radiant energy sensing means for intercepting the radiant energy emerging from the first and second chambers before it reaches the radiant energy sensing means. Signal processing means responsive to the radiant energy sensing means and the position of the chopper cells with respect to the radiant energy path provides a signal proportional to the density of the reference gas in the unknown gas sample.

11 Claims, 2 Drawing Figures

U.S. Patent  March 9, 1976  3,943,368
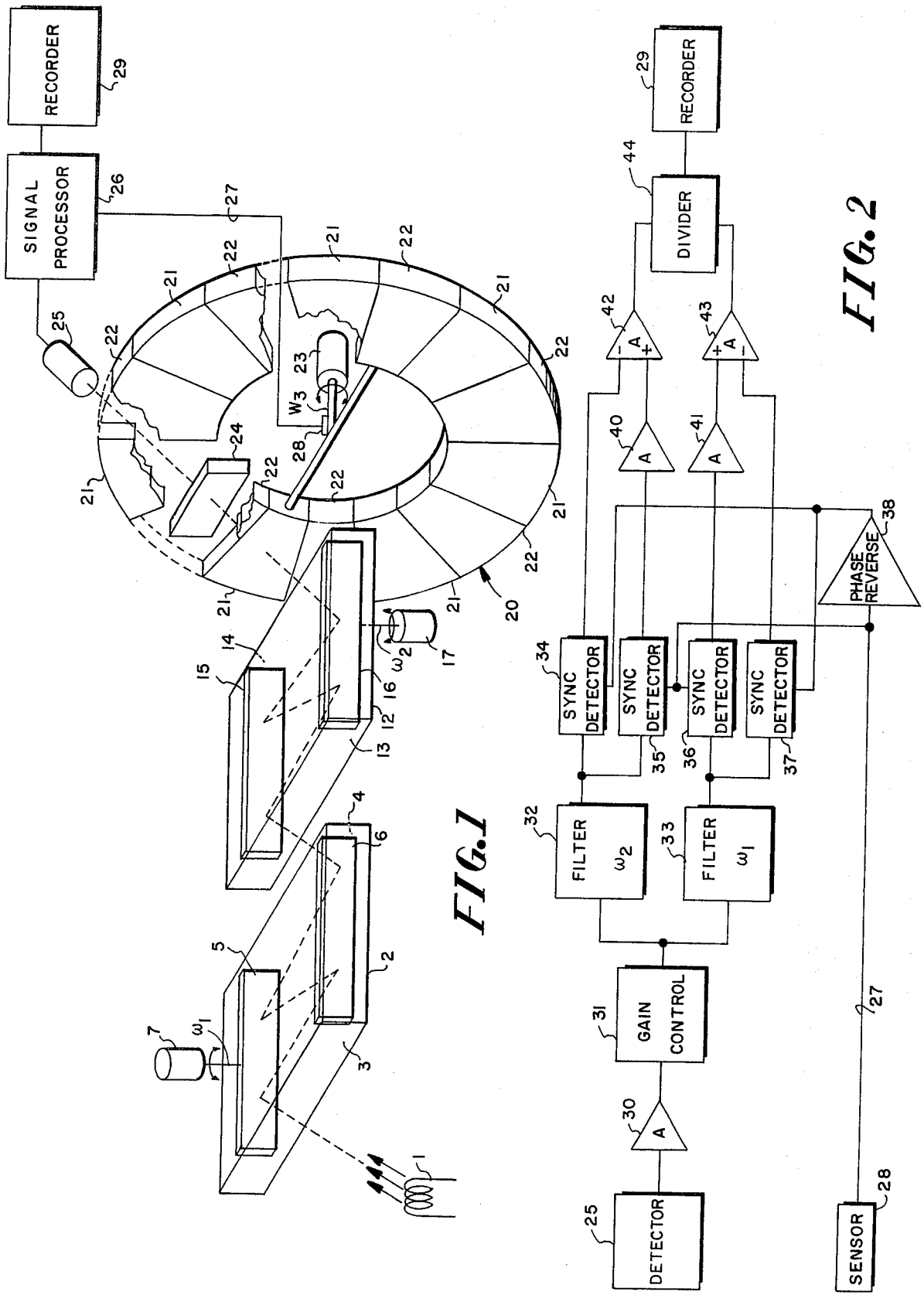

METHOD AND APPARATUS FOR COMPENSATING REFLECTION LOSSES IN A PATH LENGTH MODULATED ABSORPTION-ABSORPTION TRACE GAS

The invention described herein was made by an employee of the United States Government and may be manufactured and used by or for the Government for governmental purposes without the payment of any royalties thereon or therefor.

BACKGROUND OF THE INVENTION

The present invention relates to gas analyzing apparatus in general and in particular to an optical path length modulated absorption-absorption trace gas detection apparatus with means for providing compensation for reflection losses.

In U.S. Pat. No. 3,679,899 issued to the applicant and assigned to the assignee of the present application, there is described several techniques and apparatus for detecting trace quantities of gas by means of non-linear mixing in two samples of the gas to create a cross-correlation (or heterodyne) signal. The techniques described in the patent depend on dynamic changes of the total absorption of radiant energy in a reference gas sample and in a sample of gas containing an unknown quantity of the reference gas, with the dynamic changes being produced by changing the density of the gas samples in containers of fixed optical path length or by changing the optical path length in a pair of containers wherein the gas is maintained at a fixed density. The former technique requires relatively large volumes and powers to allow suitable fractional modulation of density. The latter technique suffers from adverse effects on signals due to the effect of variable optical geometry and the resulting effects introduced by variable reflection from the various optical surfaces involved.

SUMMARY OF THE INVENTION

In view of the foregoing, a principal object of the invention is a path length modulated absorption-absorption trace gas detection apparatus with means for reducing the effect of variable optical geometry on the signals obtained.

While the principles of the invention are applicable to both single reflection geometries and multiple reflection geometries, they will be described herein only in terms of the multi-reflection geometries, their application to single reflection geometries being readily apparent therefom.

Thus, in accordance with the present invention, there is provided, as described herein with respect to a preferred embodiment, a means forming a first chamber for containing a reference gas at a predetermined density and a means forming a second chamber for containing a sample of the reference gas at an unknown density. A radiant energy source is provided for passing radiant energy serially through the chambers. In each of the chambers, there is provided a means for modulating the length of the path of the radiant energy in the chamber at a predetermined frequency, the frequency of modulation in the two chambers being different. Located between the chambers and a radiant energy sensing means there is a chopper wheel. In the chopper wheel there are provided two sets of interleaved gas cells. One set contains a sample of the reference gas. The second set contains other gases excluding the reference gas. Means are provided for rotating the cells of each set successively into the path of the radiant energy emerging from the chambers before it reaches the radiant energy sensing means. For generating a signal proportional to the density of the reference gas in the second chamber, there is further provided, coupled to the radiant energy sensing means, a signal processing means responsive to both the output of the sensing means and the position of the chpper cells relative to the radiant energy path. The output of the signal processing means provides a signal which is proportional to the density of the reference gas in the second chamber and may also be coupled by conventional feedback circuitry to control the system gain.

DESCRIPTION OF THE DRAWINGS

The above and other objects, features and advantages of the present invention will become appaerent from the following detailed description of the accompanying drawings in which:

FIG. 1 is a block diagram of a preferred embodiment of the invention.

FIG. 2 is a block diagram of the signal processor of FIG. 1.

DETAILED DESCRIPTION OF THE INVENTION

Referring to FIG. 1, there is provided a source 1 for producing a beam of radiant energy as illustrated by three parallel arrows and a broken line. Located in a position to intercept the beam of radiant energy from source 1 is a first chamber 2 having a pair of wall members 3 and 4 which are provided to be transparent to the radiant energy. For reflecting the energy beam within chamber 2 there is provided a pair of spaced nominally parallel plane mirrors 5 and 6. Mirror 5 is coupled to a motor means 7 which may comprise a tuning fork, a galvanometer movement or other like mechanism for rotating the mirror 5 in a reciprocating fashion relative to the mirror 6 at a frequency $\omega_1$. If desired in a particular application, mirror 6 may also be moved by a means similar to motor means 7, but, in that case, it is recommended that the mirror be counterrotated relative to the mirror 5.

Adjacent to chamber 2 and in a position to intercept radiant energy emerging from chamber 2 is a second chamber 12 which is also provided with a pair of wall members 13 and 14 which are transparent to the radiant energy produced by source 1. Mounted within chamber 12 there is a pair of spaced nonimally parallel plane mirros 15 and 16. Like mirror 5, mirror 16 is coupled for rotation at a frequency $\omega_2$ which is different from $\omega_1$ to a motor means 17 which may comprise a tuning fork, a galvanometer movement or like mechanism. Similarly, if desired for a particular application, mirror 15 may also be adapted with like means not shown for counter-rotational movement relative to the mirror 16.

On the down-stream side of chamber 12, there is provided a chopper wheel 20 having disposed about its periphery in alternate locations a plurality of gas cells 21 and 22. Only a few of the cells 21 and 22 are shown for purposes of clarity. A motor means 23 is coupled to wheel 20 for rotating the cells 21 and 22 successively into the radiant energy path to intercept the radiant energy emerging from the chamber 12. Adjacent to chopper 20 and downstream therefrom there is further provided a spectrum limited filter 24 and a radiant energy sensitive photodetector 25. Detector 25 outputs an electrical signal corresponding to the radiant energy it detects. Coupled to detector 25 is a signal processor 26 which receives a control signal on a line 27 from a chopper wheel position sensing element 28 for driving a recorder 29.

Referring to FIG. 2, there is provided, in a preferred embodiment of the signal processor 26, an amplifier 30 and a gain control circuit means 31. Coupled in parallel to circuit 31 is a pair of tuned filters 32 and 33, tuned respectively to $\omega_2$ and $\omega_1$. To the output of filter 32 there is coupled a first pair of synchronous detectors 34 and 35. To the output of filter 33, there is coupled a second pair of synchronous detectors 36 and 37. To synchronize detectors 34, 35, 36 and 37, the control line 27 from chopper wheel means 20 is coupled directly to the detectors 35 and 36 and through a phase reversal circuit 38 to the detectors 34 and 37. The control signal generated by element 28 is an on-off signal phased with the positions of the gas cells 21 and 22. To the output of detectors 35 and 36 there is coupled, respectively, an amplifier 40 and 41. The output of amplifier 40 and detector 34 is coupled to a difference amplifier 42. The output of amplifier 41 and detector 37 is coupled to a difference amplifier 43. A divider circuit 44 is further provided for receiving the outputs of amplifiers 42 and 43 for driving the recorder 29.

In operation, a reference gas of interest is received in chamber 2 having a predetermined partial density. A sample of gas, which may include an amount of the reference gas but having an unknown partial density, is received in chamber 12. Gas cell 21 in chopper wheel 20 is filled with a predetermined sample of the reference gas and a suitable admixture of other gases. Gas cell 22 is filled only with the admixed gases. Valve means for filling and emptying chambers 2 and 12 and gas cells 21 and 22 are conventional and consequently are not illustrated.

Once the chambers and cells are filled, radiant energy from source 1 is directed through the chambers to the detector 25. The mirrors 5 and 16 are moved in a reciprocating movement for modulating the length of the path of the radiant energy in the chambers at the angular frequencies $\omega_1$ and $\omega_2$, respectively, and chopper wheel 20 is rotated at an angular frequency $\omega_3$. The frequencies $\omega_1$, $\omega_2$ and $\omega_3$ are chosen such that $\omega_1$ and $\omega_2$ are different one from the other and high compared to the chopper frequency $\omega_3$. During the time that chopper cell 21 is in the optical path and depending on the density of the reference gas contained therein, it absorbs all, or at least a portion of the radiant energy in the spectral regions normally affected by the reference gas in chambers 2 and 12. The detected intensity variations occurring at $\omega_1$ and $\omega_2$, therefore, provide information on the intensity variations introduced by reflection losses within the chambers 2 and 12, respectively. When the chopper wheel is rotated so that the light beam traverses cell 22 before impinging on the detector 25, the signals obtained at $\omega_1$ and $\omega_2$ provide information on the combined effect of mirror reflection and gas absorption in the chambers 2 and 12, respectively. When properly combined, these signals provide an indication on the recorder 29 which is proportional to the density of the reference gas in the chamber 12.

More analytically, the light intensity impinging on the photodetector 25 of the apparatus described above can be computed from the equation $$I = I_0 R_2^n R_{12}^m e^{-\mu \rho_n x_n e - \mu \rho_m x_m m} \qquad (1)$$

where $I_0$ is the average intensity of the light impinging on the photodetector and is wavelength dependent, $R_2$, $R_{12}$ are the average reflection coefficients of the mirror systems 5, 6 and 15, 16 within chambers 2 and 12, respectively.

$n$, $m$ are the number of additional reflections resulting from displacement of the mirrors 5 and 16 from their average position in chambers 2 and 12, respectively, $\mu$ is the mass absorption coefficient of the reference gas of interest, $\rho_n$, $\rho_m$ are the densities of the reference gas of interest in chambers 2 and 12, respectively, and $x_n$, $x_m$ are the changes in the path lengths of the beams. The equation (1) can be rewritten in the form $$I = I_0 \exp\ [(n\ \ln\ R_4 - \mu \rho_n x_n)_{\omega_1} + (m\ \ln\ R_6 - \mu \rho_m x_m)_{\omega_2}] \qquad (2)$$

where the subscript $\omega$ is a reminder that all terms within the served parenthesis are modulated at the angular frequencies, $\omega_1$ and $\omega_2$, of the respective mirrors.

If it is assumed that the fluctuations are small, one may approximate the exponential by using the expression $$e^\Delta \approx 1 + \Delta \qquad (3)$$

and rewrite the equation for light intensity in the form $$I \approx I_0\ [1\ +\ (n\ \ln\ R_4 - \mu \rho_n x_n)_{\omega_1} + (m\ \ln\ R_6 - \mu \rho_m x_m)_{\omega_2}] \qquad (4)$$

If one separates the intensity into its frequency components as by the use of appropriate electronic filters, one may write $$I_{\omega_1} = I_{01} n\ \ln\ R_4 + I_{02}\ (n\ \ln\ R_4 - \mu \rho_n x_n) \qquad (5)$$

for the intensity variation at $\omega_1$ and $$I_{\omega_2} = I_{01} m\ \ln\ R_6 + I_{02}\ (m\ \ln\ R_6 - \mu \rho_m x_m) \qquad (6)$$

for the intensity variation at $\omega_2$
where $I_{01}$ is the intensity of that portion of the emergent light beam in the spectral region which is not affected by the reference gas to be measured and $I_{02}$ is the portion which is in the affected spectral region.

For the case wherein cells 21 contain an optically thick sample of the reference gas for 100% absorption of the spectral lines normally affected by the reference gas such that chopper wheel 20 introduces a periodic modulation which causes $I_{02}$ to be zero during the times when the sample of the reference gas in cell 21 is in the ray path (the measured intensities during those times being designated by the superscript$^0$) and allows $I_{02}$ to reach its normal value during the intervening periods (the measured intensities during these periods being designated by the superscript$^1$), one may write $$I_{\omega_1}{}^0 - I_{\omega_1}{}^1 = -I_{02}\ (n\ \ln\ R_4 - \mu \rho_n x_n) \qquad (7)$$

and $$n\ \ln\ R_4 = I_{\omega_1}/I_{01}$$

Combining the above, one obtains $$I\omega_1{}^0 - I\omega_1{}^1 = -\frac{I_{02}}{I_{01}} I\omega_1{}^0 + I_{02}\, \mu\rho_n x_n \quad (8)$$

$$\text{or } \mu\rho_n x_n = \frac{I\omega_1{}^0 \left(1 + \frac{I_{02}}{I_{01}}\right) - I\omega_1{}^1}{I_{02}} \quad (9)$$

One may write, similarly $$\mu\rho_m x_m = \frac{I\omega_2{}^0 \left(1 + \frac{I_{02}}{I_{01}}\right) - I\omega_2{}^1}{I_{02}} \quad (10)$$

and solve these two equations simultaneously to give $$\rho_m = \rho_n \left(\frac{x_n}{x_m}\right) \left[\frac{I\omega_2{}^0 \left(1 + \frac{I_{02}}{I_{01}}\right) - I\omega_2{}^1}{I\omega_1{}^0 \left(1 + \frac{I_{02}}{I_{01}}\right) - I\omega_1{}^1}\right] \quad (11)$$

For a particular optical geometry and for a particular set of mirror drive amplitudes, the ratio of $X_n$ to $X_m$ is constant. Variation of relative drive amplitude allows a mechanism for "nulling" the response in conformance with normal feedback control practices (the calibration in this instance being derived from the relative magnitudes of the mirror drives required for balance) or a mechanism for adjusting the instrument gain.

The ratio of $I_{02}$ to $I_{01}$ is dependent only on the spectral distribution of the light source, and the distribution of the absorption spectrum of the reference gas of interest, and, while it must be calibrated for the particular instrument configuration, remains constant.

While the above discussion has described the instrument in terms of chambers involving nominally parallel mirrors with oscillations imposed on the angle therebetween, spherical chambers may be substituted therefor. In such an arrangement, each chamber has a mirrored interior. A portion of the interior of each chamber is provided with a chopping device that alternately reflects and passes (or absorbs) the radiation impinging thereon. The chopping device may comprise a window with an oscillating mirror therebehind which periodically passes by the window and reflects the radiation falling thereon. Alternatively, a spinning disk with alternate reflective and non-reflective segments may be positioned by the window in place of the oscillating mirror so that radiation is periodically reflected. Radiation admitted to the first spherical chamber is reflected from the walls and the chopping device and allowed to enter the second spherical chamber. In the second spherical chamber the radiation is reflected from the walls and the second chopping device before it passes through chopper wheel 20 and impinges on detector 25.

Each chamber might also be configured as a "White Cell" using confocal mirrors with the number of passes therebetween controlled by angular modulation of one of the mirrors.

In addition to the various optical geometries, the electrical processing of the signal can proceed according to various options. It is apparent from the equation that the density to be measured $\rho_m$ is proportional to the ratio of the amplitudes of the signals modulating the frequencies $\omega_2$ and $\omega_1$ respectively. In accordance with the teachings, for example of U.S. Pat. No. 3,679.899, it is possible to repeat the analysis above looking at higher order terms in the series expansion for the exponential (that is at the terms $\Delta^2/2! + \Delta^3/3! - - -$ dropped from the approximation) using harmonics of the drive frequencies or sum and difference frequencies generated by the non-linear absorption process.

In each instance, however, it is apparent that the disclosed device provides the highly desirable features of:

a. Specificity — since the mathematics assume that the chopper wheel filter, the reference and the unknown gas chambers all operate on the same detailed spectrum, b. Stability — since the equation for density of the unknown gas does not depend on the intensity of the light source or an attenuation of the beam by window fogging, etc., c. Sensitivity — since it is possible to use the fundamental frequency of the absorption signal rather that the higher (and smaller amplitude) harmonics, and since large modulations of path length can be achieved, and d. Simplicity — since the signal levels are higher, and the mechanical work required to produce a significant periodic tilting of the mirrors is considerably less than the mechanical work required to produce a significant periodic change in the density of a gas through compression.

Although other modifications of the present invention will undoubtedly become apparent to those skilled in the art after having read the above disclosure, it is understood that the appended claims are to be interpreted as covering all such embodiments and subsequent modifications which fall within the true spirit and scope of the invention.

What is claimed is:

1. A modulated optical path length analyzing apparatus comprising:
   means forming a first chamber for containing a reference gas at a predetermined density;
   means forming a second chamber for containing a sample of said reference gas at an unknown density;
   a source of radiant energy;
   said chambers each having an entrance and exit wall that is transparent to said radiant energy;
   said first chamber being arranged between said radiant energy source and said second chamber so that radiant energy from said radiant energy source passes through said entrance and exit walls of said first chamber before it passes through said entrance and exit walls of said second chamber;
   means for modulating the length of the path of said radiant energy in said first and said second chambers at a first and a second frequency, respectively;
   chopper means including a first cell for containing a first gas including an optically thick sample of said reference gas sufficient to absorb all of the radiant energy emerging after passage through said first and said second chambers in the spectral regions normally affected by said reference gas and a second cell for containing a second gas excluding said reference gas;
   means for periodically positioning said first and said second chopper cells in the path of said radiant energy emerging after passage through said first and said second chambers; and means responsive to the radiant energy emerging from said chopper cells and the position and said chopper cells with respect to said radiant energy path for generating a signal proportional to the density of said reference gas in said second chamber.

2. A gas analyzing apparatus according to claim 1 wherein said modulating means comprises at least one pair of facing surfaces for reflecting said radiant energy therebetween in each of said first and said second chambers and means for moving at least one of said surfaces relative to the other in each of said pairs at said first and said second frequencies respectively.

3. A gas analyzing apparatus according to claim 2 wherein said means for moving said reflecting surfaces comprises means for moving said surfaces in a reciprocating fashion.

4. A gas analyzing apparatus according to claim 3 wherein said moving of said surfaces in a reciprocating fashion comprises rotating said surfaces about an axis parallel with said surfaces.

5. A gas analyzing apparatus according to claim 4 wherein said reflecting surfaces comprise surfaces on a mirror means.

6. A gas analyzing apparatus according to claim 1 wherein said means for positioning said chopper cells comprises means for rotating said first and said second chopper cells into said radiant energy path at a third frequency.

7. A gas analyzing apparatus according to claim 6 wherein said means for positioning said chopper cells further comprises means for rotating said first and said second chopper cells into said radiant energy path successively at a third frequency which is lower than said first and said second frequencies.

8. A gas analyzing apparatus according to claim 1 wherein said signal generating means comprises:
a radiation sensing means responsive to the radiant energy from said chopper cells for providing an electrical signal containing a first and a second component at said first and said second frequencies;
means coupled to said sensing means for filtering out of said electrical signal said first and said second frequency components;
means including detecting means coupled to said filtering means and responsive to the position of said chopper cells with respect to said radiant energy path for detecting said first and said second frequency components when each of said chopper cells is in said radiant energy path;
means including a subtracting means coupled to said detecting means for providing a first signal proportional to the difference in the amplitude of said first frequency component when said first and said second chopper cells are in said radiant energy path and a second signal proportional to the difference in the amplitude of said second frequency component when said first and said second chopper cells are in said radiant energy path; and
means including a dividing means coupled to said subtracting means for providing a signal proportional to the ratio of said difference signals at said first and said second frequencies.

9. A gas analyzing apparatus according to claim 1 wherein said predetermined sample of said reference gas in said first cell of said chopper means comprises an optically thick sample of said reference gas sufficient to absorb substantially all of the radiant energy emerging after passage through said first and said second chambers in the spectral regions normally affected by said reference gas.

10. A gas analyzing method comprising the steps:
providing a quantity of a reference gas and a quantity of an unknown gas removed therefrom; directing radiant energy serially, in time and space, through said reference gas and said unknown gas in such a manner that said radiant energy is at least partially absorbed in passing therethrough;
modulating the absorption of said radiant energy in said reference and said known gases by periodically varying the length of the path taken by said radiant energy in passing through said gases at a first and a second frequency, respectively;
periodically absorbing the radiant energy modulated at said first and said second frequencies after passage through said reference and unknown gases in the spectral regions normally affected by said reference gas and in the spectral regions normally unaffected by said reference gas at a third frequency; and
detecting the radiant energy after said periodic absorption at said third frequency for developing an electrical signal proportional to the density of said reference gas in said unknown gas.

11. A method according to claim 10 wherein said step of periodically absorbing the radiant energy modulated at said first and said second frequencies comprises periodically absorbing at said third frequency substantially all of the radiant energy in the spectral regions normally affected by said reference gas and, at least partially, the radiant energy in the spectral regions normally unaffected by said reference gas.

* * * * *